United States Patent [19]

Klemm

[11] Patent Number: Plant 7,016

[45] Date of Patent: Sep. 5, 1989

[54] GERANIUM NAMED KLEDAP

[76] Inventor: Siegfried Klemm, Hanfacker 8, D-7000 Stuttgart 50, Fed. Rep. of Germany

[21] Appl. No.: 244,311

[22] Filed: Sep. 15, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new and distinct geranium variety particularly distinguished by its bright red flowers of noble form displayed above a bushy, compact foliage body and providing a medium sized plant of about 33 to 55 cm. in total height above the soil. This new plant is very floriferous, blooming continuously and profusely from early spring to late Fall and providing a succession of many round flower clusters, each including about eighty individual florets. This plant has a vigorous, compact and bushy growth habit with a medium growth rate and presenting flower clusters which have petals remaining on the stem from about thirteen to fourteen days.

1 Drawing Sheet

BACKGROUND OF THE NEW PLANT

My new geranium variety originated in 1985 as a seedling of a hybrid resulting from my crossing of the variety 'PAC Isabell' (unpatented) with the pollen of the variety 'Osna' (unpatented) at my nursery at Stuttgart, West Germany, with the object of producing very floriferous, early blooming plants having flowers that are double and all of the same shape. The present seedling, having substantially the characteristics that I desired, was propagated by me and under my direction at Stuttgart, by means of cuttings, through several successive generations, which demonstrated conclusively that its novel characteristics would remain true from generation to generation and appeared to be firmly fixed. Due to the bright color and the nice foliage of this new geranium variety and the fact that it is weatherproof, its market value is high.

DESCRIPTION OF THE DRAWING

My new geranium variety is illustrated by the accompanying full color photographic drawing, which shows a potted plant of my new variety having flower clusters in full bloom and showing the plant form, the nature of its foliage, and bud clusters in various stages of development. The colors shown are as true to those herein specified as can resonably be obtained by conventional, professional photographic procedures.

DESCRIPTION OF THE NEW PLANT

Figure 1:
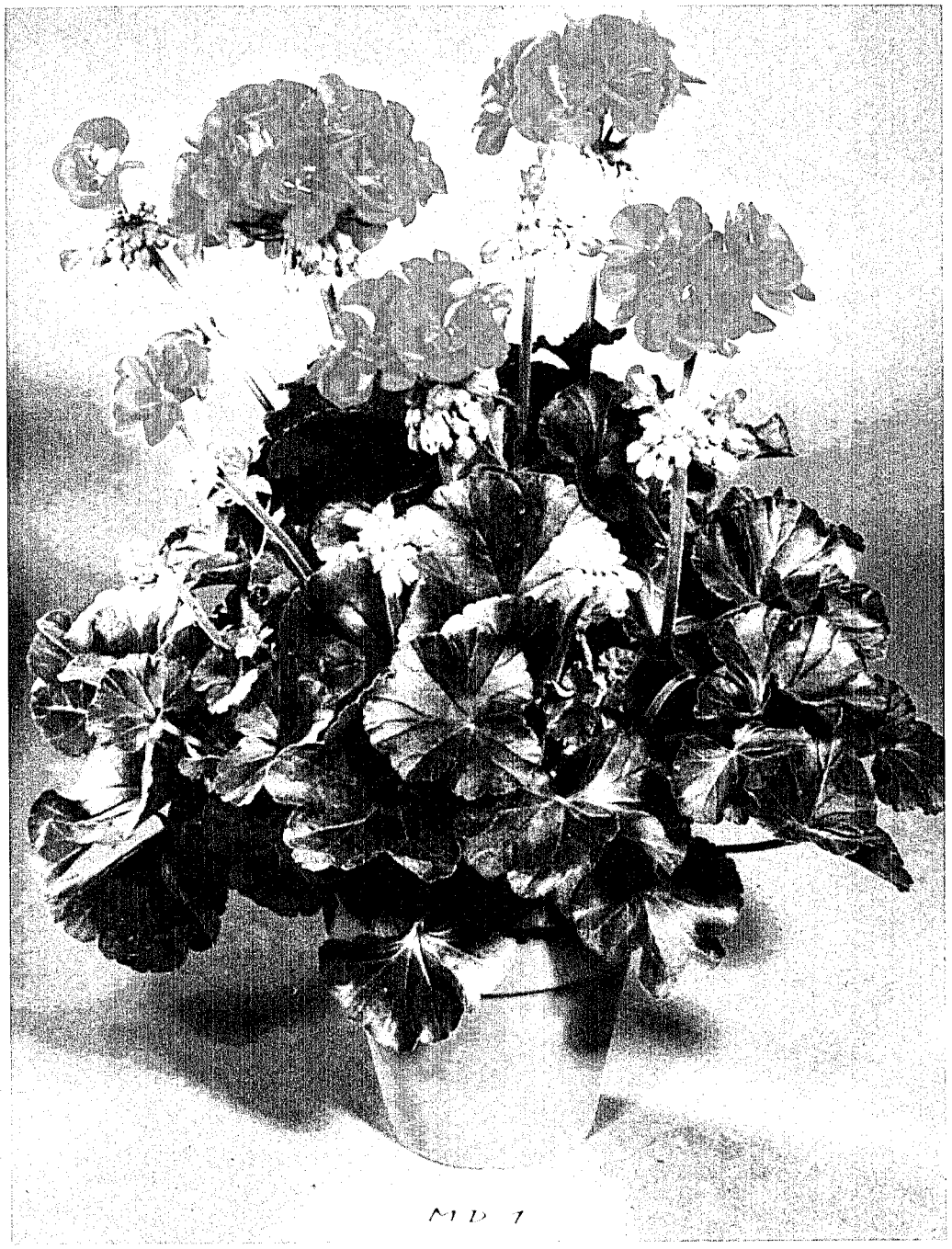

The following is a detailed description of my new geranium cultivar as observed of plants grown indoors and outdoors at Stuttgart, West Germany, with the color designations being according to The R.H.S. Colour Chart of The Royal Horticultural Society of London, England.

THE PLANT

Origin: Seedling.

Parentage:

*Seed parent.*—'PAC Isabell' (unpatented).

*Pollen parent.*—'Osna' (unpatented).

Classification:

*Botanic.*—*Pelargonium zonale* hybrid.

*Commercial.*—Geranium.

Form: Bushy and compact.

Height: Medium; about 35 cm. above the soil.

Flower stem length: About 15 cm.

Branching character: Very good.

Growth: Vigorous, bushy and compact with good strength and stability.

Foliage:

*Quantity.*—Moderately abundant.

*Size of leaf.*—From about 6×7 cm. to about 7×7 cm.

*Leaf shape.*—Reniform with bicrenate margins.

Texture.—Smooth.

Ribs and veins.—Five main veins on each leaf.

*Color.*—Upper side — Medium Green with little zonation. Under side — Light Green.

THE BUD

Size: Medium.

*Diameter.*—About 11 mm.

*Length.*—About 14 mm.

Shape: Generally ovoid with pointed apex.

Opening rate: Medium.

Color:

*When sepals first divide.*—Light Red.

*When petals begin to unfurl.*—Red.

Sepals:

*Shape.*—Linear.

*Number.*—Five.

*Character.*—The sepals stand up when the flowers open.

Color.—Green, inside and outside.

Flower stem:

*Length.*—About 15 cm.

*Character.*—Rigid, upright and very strong.

*Color.*—Medium Green.

THE INFLORESCENCE

Blooming habit: Continuous and profusely from early Spring to late Fall.

Cluster:

*Size.*—Large.

*Shape.*—Round.

*Number of florets.*—About 80.

Florets:

*Size.*—Medium. Diameter — About 4 cm. Depth — About 1 cm.

*Borne.*—Singly on the umbel stem of a cluster.

*Shape.*—When bloom first opens, cup-shaped. When bloom matures, flat.

Petalage:

*Number of petals.*—Eight to ten.

*Arrangement.*—Imbricated.

*Form.*—Broad ovate with entire margin and round apex.

*Texture.*—Soft.

*Appearance.*—Velvety.

*Color.*—Red, R.H.S. 34-A.

Effect of weather: Very little.

Lasting quality: On the plant, the flower lasts about fourteen days.

REPRODUCTIVE ORGANS

Stamens:

*Number.*—Seven.

*Arrangement.*—In a ring.

*Anthers.*—Size: About 1.7 mm. Color: Orange.

*Filaments.*—Length: About 4 mm. Color: White.

*Pollen.*—Color: Orange.

Pistil:

*Number.*—One.

*Style.*—Length: About 5 mm. Color: White Pink.

*Stigma.*—Five cells. Color: Frosted Pink Glas.

Character of ovaries: Normal.

THE FRUIT

Fertility: The fruit is fertile.

Shape: Ovoid.

Color at maturity: Dark Brown.

The color of this variety is like that of 'Bundeskanzler'. However, this new variety is very floriferous and starts blooming early in the Spring, the flowers are double and all of the same shape. The plant growth is low and bushy and as a potted plant, its appearance is perfect.

I claim:

1. The new and distinct geranium cultivar, as herein shown and described, particularly distinguished by the bright red color of its flower clusters and the bushy, compact growth of its foliage underlying the inflorescence presentation.

* * * * *